United States Patent [19]

McAdoo et al.

[11] Patent Number: 5,754,055

[45] Date of Patent: May 19, 1998

[54] LUBRICATING FLUID CONDITION MONITOR

[75] Inventors: John H. McAdoo, McClean; William Catoe, Woodbridge; Michael W. Bollen, Clifton; Vince Folen, Alexandria, all of Va.; Fred Volkening, Boonsboro, Md.

[73] Assignee: Mission Research Corporation, Santa Barbara, Calif.

[21] Appl. No.: 582,646

[22] Filed: Jan. 4, 1996

[51] Int. Cl.⁶ .................... G01N 22/02; G01N 33/30; F01M 11/10
[52] U.S. Cl. .................... 324/636; 324/553; 324/638; 324/637; 324/639; 340/631; 73/61.42
[58] Field of Search .................... 324/553, 602, 324/603, 630, 633, 636, 637, 639, 647; 340/603, 627, 631; 73/61.42

[56] References Cited

U.S. PATENT DOCUMENTS

| 2,810,882 | 10/1957 | Walker | 324/633 |
|---|---|---|---|
| 4,829,233 | 5/1989 | Flemming et al. | 324/633 |
| 4,909,081 | 3/1990 | Kulczyk et al. | 73/61.42 X |
| 5,025,222 | 6/1991 | Scott et al. | 324/639 |
| 5,101,163 | 3/1992 | Agar | 324/639 |
| 5,157,337 | 10/1992 | Neel et al. | 324/633 |
| 5,262,732 | 11/1993 | Dickert et al. | 324/553 X |
| 5,343,150 | 8/1994 | Nakahata et al. | 324/633 |
| 5,373,244 | 12/1994 | Marrelli | 324/647 X |
| 5,382,942 | 1/1995 | Raffa et al. | 340/457.4 |
| 5,383,535 | 1/1995 | Marrelli et al. | 324/639 X |
| 5,389,883 | 2/1995 | Harper | 324/636 |
| 5,455,565 | 10/1995 | Moeenziai et al. | 340/603 |
| 5,485,083 | 1/1996 | Pulice | 324/633 |
| 5,614,830 | 3/1997 | Dickert et al. | 324/553 |

*Primary Examiner*—Glenn W. Brown
*Attorney, Agent, or Firm*—David O'Reilly

[57] ABSTRACT

A lubricating/hydraulic fluid condition monitor in which a coaxial microwave resonator is placed in a fluid conduit to determine changes in the chemical properties and debris concentration is disclosed. Microwave radiation is applied to the resonator for measuring the resonant frequency and resonator Q. An externally powered electric or magnetic field is used to alternately align and misalign debris in the fluid while the resonator properties are being measured. A logic unit automatically generates tables of resonant frequency and Q versus resonator mode and external field strength. This set of tables constitutes a fingerprint of the fluid condition. By matching the fingerprint against a set of fingerprints taken under known conditions, the condition of the fluid is determined. Changes in the fluid's dielectric constant caused by oxidation or the presence of water, changes in the concentration and size of conducting particles from bearing wear, and changes in viscosity all affect the fingerprint; and thus, can be monitored in real time. In a variation of the invention, a lumped-circuit resonator printed on a microwave circuit board is used as the sensor. In a further variation, a transmission-line resonator printed on a microwave circuit board is used as a sensor. In yet another variation the resonator is a lumped circuit waveguide structure through which the fluid flows. In still another variation, time domain reflectometry is used in a transmission line having one end immersed in the fluid.

9 Claims, 2 Drawing Sheets

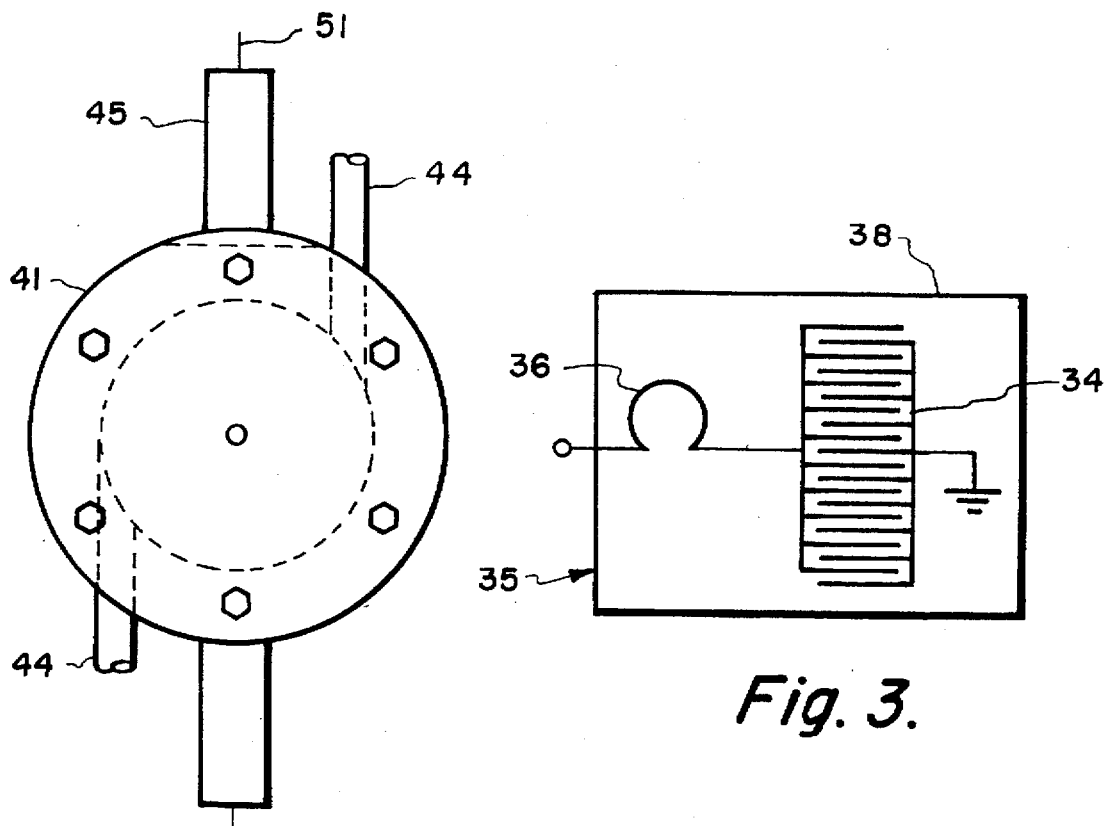
Fig. 2.
Fig. 3.
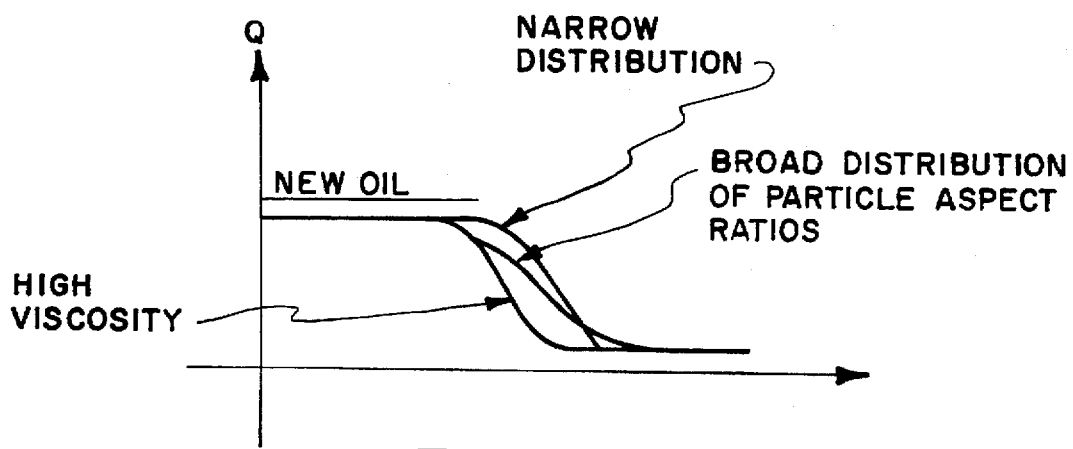
Fig. 4.

LUBRICATING FLUID CONDITION MONITOR

BACKGROUND OF THE INVENTION

1. Field of the Invention

This invention relates to systems and methods for monitoring lubricating fluids or hydraulic fluids for contaminates and more particularly, relates to a lubricating/hydraulic fluid condition monitor that measures metal particle contamination, fuel and water contamination, changes in detergent concentration, changes in antioxidant concentration and changes in viscosity.

2. Background Information

The ability to predict potential mechanical component failures before they occur would be useful in many industries, particularly the aircraft industry. Presently, lubricating fluids are tested for signs of engine stress. Expenditure of additives, the presence of water, and changes in the concentration of metal particles can signal a problem in time to take corrective action. To provide this function, present methods involve examination of wear debris in lubricating fluid and the chemical properties of the fluid in a laboratory during routine maintenance. The only in-line monitors presently in wide-spread use are magnetic chip detectors, which are inadequate.

Ideally, instruments that can detect changes in lubricating/hydraulic fluids in real-time should be part of an engine or hydraulic system, and should be capable of signifying sudden changes in trends within seconds of their occurrence. Such an instrument would provide an airline pilot sufficient warning to land the aircraft prior to catastrophic failure of the engine. No suitable instruments are presently available to perform this task.

Present techniques for lubricating oil have been developed by others to indicate when an oil change is necessary and to predict the on-set of engine problems in time to make repairs in order to prevent catastrophic breakdowns. As oil ages in a working engine, its chemical make-up changes as well as its physical make-up. Chemical changes are dominated by oxidation reactions accelerated by heat. Physical changes are dominated by an increase in the concentration of suspended wear particles from bearings or the presence of water in marine hydraulic systems and water cooled engines.

Various techniques have been used to detect changes in chemical make-up. These are chemiluminescence, emission and absorption spectroscopy (including infrared spectroscopy, voltammetry, acidmetry and dielectric constant measurements). Techniques commonly used to detect changes in the make-up of wear particles include ferrography, emission spectroscopy, magnetic chip detection, x-ray fluorescence, ultrasonic reflectometry and induction techniques. Of these techniques, only the magnetic chip detection has been developed for onboard monitoring of lubrication oil, but it is insensitive to particles smaller than a few hundred micrometers; and thus, can not perform the task of reliably monitoring lubricating fluids in real-time. No instrument is presently known that is suitable for installation in working engines to provide real-time monitoring of the condition of lubricating fluid.

It is therefore, one object of the present invention, to provide a lubricating fluid condition monitor that can (in real-time) monitor, display and record chemical properties, a spectrum of particle sizes, and oil viscosity with a single sensor requiring the barest modification to existing plumbing.

Another object of the present invention is to provide a portable instrument for field use that can monitor and record the condition of lubricating/hydraulic fluids.

Another object of the present invention is to provide a lubricating fluid condition monitor that can monitor the condition of lubricating/hydraulic fluids with a single sensor by using microwave frequencies.

Still another object of the present invention is to provide a lubricating fluid condition monitor that can use a single resonator to form the task of measuring both changes in the chemical makeup and changes in the physical properties of a lubricating/hydraulic fluid.

Still another object of the present invention is to provide a lubricating fluid condition monitor with improved sensitivity to measure changes in the dielectric constant of the fluid.

Yet another object of the present invention is to provide a lubricating fluid condition monitor that can utilize high-frequency microwaves to provide a single sensor much smaller in size than presently available.

Yet another object of the present invention is to provide a lubricating fluid condition monitor that utilizes a microwave resonator in the fluid plumbing to monitor the condition of the fluid.

Still another object of the present invention is to provide a lubricating fluid condition monitor using a microwave resonator to measure complex dielectric constant of an oil-particle mixture and viscosity, and distinguish changes in aspect ratio and size distribution of conducting particles.

Still another object of the present invention is to provide a lubricating fluid condition monitor using a microwave transmission line or stripline as a sensor to measure lubricant properties by a change of the impedance of the transmission line.

Yet another object of the present invention is to provide a lubricating fluid condition monitor that uses a stripline resonator comprised of an inductor and a capacitor printed on a circuit board as a sensor.

Yet another object of the present invention is to provide a lubricating fluid condition monitor comprised of a stripline resonator that determines the properties of a lubricating fluid by measuring the resonant frequency and Q when immersed in the lubricating fluid.

Another object of the present invention is to provide a lubricating fluid condition monitor comprised of a sealed transmission line having one end open to radiation but sealed to fluid. That end of the line is immersed in the fluid to be characterized. A voltage pulse with a duration much less than the transit time through the line is sent to the immersed end. Using the well-known techniques of time domain reflectometry, the properties of the fluid are thus determined.

BRIEF DESCRIPTION OF THE INVENTION

The purpose of the present invention is to provide an instrument that can monitor the condition of an engine or hydraulic system and warn of impending failure by continuously analyzing lubrication/hydraulic fluids. Unusual changes in the composition of additives, the concentration of metal particles, or the appearance of water will trigger a warning in an operating machine. Maintenance crews will also use the invention to determine maintenance action in a more timely manner than is now provided by the routine analysis of fluids by laboratories.

The present invention provides a means for monitoring, displaying and recording real-time changes in the following aspects of a lubricating fluid: antioxidant composition, detergent composition, water content, metal particle content and viscosity. In addition the invention can roughly determine the spectrum of metal particle sizes. The invention uses a single sensor that requires minimum modification to existing plumbing. The lubricating fluid condition monitoring system is comprised of a miniature microwave resonator, positioned in the flow of lubricating/hydraulic fluid, with means for applying either an electric or magnetic field across the resonator axis. External electronics, connected to the microwave resonator, are comprised of integrated circuits and microprocessor chips. The system measures complex dielectric constants of the fluid-particle mixture. The externally applied field permits the monitoring of viscosity and the drawing of inferences on the spectrum of metal particle sizes and aspect ratios.

The information on the condition of the lubricating fluid is obtained from two continuously monitored resonator parameters: The width of the resonance line (the resonator Q) and the resonant frequency. The resonator's Q is sensitive to the imaginary part of the effective electric and magnetic susceptibilities which will primarily depend upon the concentration of conductive particles. The resonant frequency is most sensitive to the real part of the dielectric constant of the lubricant, as well as the real part of the effective electric and magnetic susceptibilities of the conducting particles. A substantial increase in obtainable information is achieved by alternating the electric field while monitoring the resonator Q and the resonant frequency.

The field modulates the complex dielectric constant of the oil-metal mixture by alternately aligning and misaligning the asymmetrical shaped conductive/magnetic debris. The amplitude of modulations depends on the concentration and shape of conductive/magnetic particles. The viscosity of the oil is monitored because the viscosity effects the time required for particles to change alignment (or relax) and relaxation time is measured by varying the electric field's modulation frequency.

The resonator is small and light enough to fit inside an aircraft lubrication system with minimal modification by using frequencies that can be achieved with an integrated circuit the size of a typical wear particle. The largest part of the system would be the resonator itself, comprised of a cylinder whose dimensions are similar to the wavelength of the microwave radiation employed. At 10 GHz, the wavelength is approximately 3 cm; thus, the resonator is similar in size to a chip detector. Outside the lubricating-oil system, a small electronic package containing the microwave oscillator, power supply for external field devices and microprocessor energizes the sensor and interprets the signals received. The microwave system is low in power and completely shielded to eliminate interference with avionics.

A first embodiment of the invention employs a coaxial microwave resonator in the flow of oil from parts being lubricated to a lubricating fluid sump tank. A microwave-oscillator energized sensor and a logic unit, connected to the sensor, will measure the resonator frequency and Q to detect changes in dielectric properties of the non-conducting lubricating fluid.

A second embodiment uses a stripline on a printed circuit board as the sensor. The properties of surrounding materials affect the impedance of transmissions on the stripline. When the stripline is placed in the path of a lubricant, the real and imaginary parts of the impedance are altered. This alteration causes the phase and intensity of the microwaves reflected from the stripline to change. Measurement of the phase and intensity changes enable the lubricant properties to be determined.

A third embodiment uses a microstrip resonator, comprised of a circuit consisting of an inductor and a capacitor printed on a circuit board. The inductor consists of a single loop, spiral, or meander line; and the capacitor consists of interdigitated conductors. Since the inductance and capacitance of the resonator elements are affected by the properties of the lubricating fluid in which the circuit is immersed, the resonant frequency and Q are similarly affected. A distinct advantage of the use of the microstrip resonator is that the overall size can be substantially reduced which will expand the number of applications suitable for the sensor.

A fourth embodiment uses a section of unterminated stripline as a resonator. The Q and resonant frequency of the line will be affected by the fluid in which the line is immersed.

A fifth embodiment uses a lumped-circuit resonator. These are hollow metal structures like waveguide resonators. Unlike waveguide resonators, inductive and capacitive regions are clearly identifiable as separate, but connected structures. An example would be a coaxial cylinder in which the center solid cylinder was connected to one end wall of the outer cylinder. The other end of the inner cylinder stops just short of the opposite end wall of the outer cylinder. The gap between the end of the inner cylinder and the end wall of the outer cylinder forms a capacitor, while the inner cylinder is an inductor. Lumped-circuit resonators can resonate at much lower frequencies for a given size than can their waveguide counterparts.

The embodiments described above, the concept of using an electric field, magnetic field or both to change the orientation of asymmetrical wear plane products in the vicinity of sensors, is very useful. Measurement of these changes provides a way to determine fluid viscosity, distribution of particle sizes and whether the particles are ferrous or nonferrous conducting particles.

The above and other novel features of the invention will be more fully understood from the following detailed description and the accompanying drawings, in which:

BRIEF DESCRIPTION OF THE DRAWINGS

FIG. 2 is an end view of the coaxial microwave resonator in FIG. 1.

FIG. 3 is a diagram of a sensor consisting of an interdigitated capacitor and inductor printed on a circuit board.

FIG. 4 is a graph illustrating the change in resonator Q as a function of the frequency of alternating external field applied to align asymmetric particles in the lubricating fluid.

DETAILED DESCRIPTION OF THE INVENTION

Figure 1:
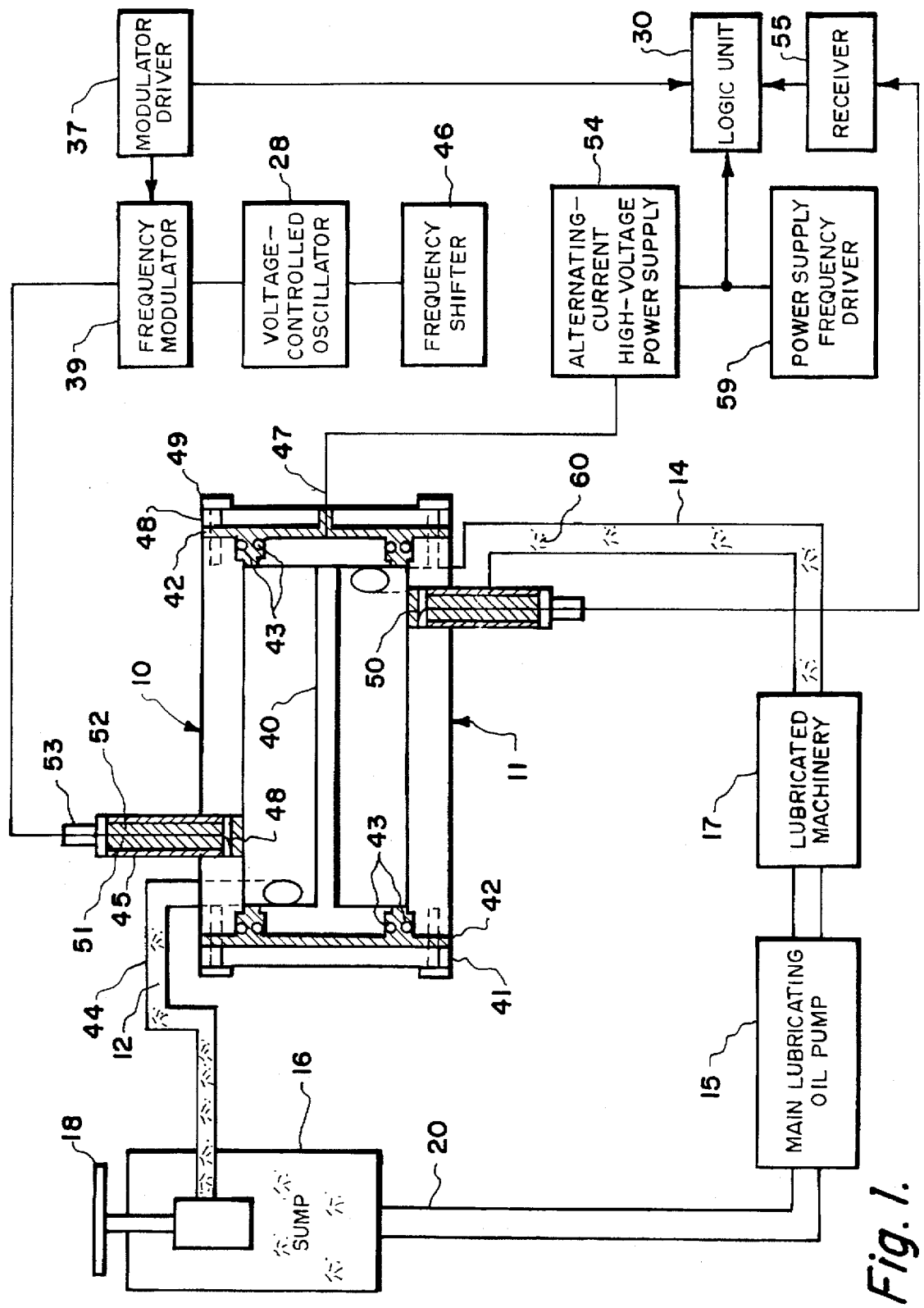
FIG. 1 is a schematic block diagram of a lubricating fluid condition monitor using a coaxial microwave resonator as sensor.

A lubricating fluid condition monitor, having a coaxial microwave resonator, is generally shown in the schematic block diagrams of FIG. 1. Coaxial microwave resonator 10 is positioned in the flow of lubricating fluid 12, flowing through conduit 14. Lubricating fluid 12 flows into sump tank 16 through aerator 18, and to main lube oil pump through conduit 20. Coaxial microwave resonator 10, shown in FIG. 1, is comprised of cylinder 11, capped with end walls 41 and 41'. A center conductor 40 is held in place by a low-loss insulator 42. O-rings 43 form a seal preventing the fluid from permeating the space around insulator 42. Insulator 42 is thin enabling the microwave currents generated in center conductor 40 to couple capacitatively to end walls 41, 41'. End walls 41, 41' together with bolts 49 compress O-rings 43 to form a seal. Wire 47 is connected to the center conductor 40 and passes through an insulated hole in end wall 41'. Wire 47 is used to charge the center conductor 40 to several kilo-volts with high-voltage power supply 54. Microwave power is coupled into the resonator via wire loop 50 and wire lead 51. The lead together with housing 45 and insulator 52 form a standard microwave transmission line terminated by standard connector 53. Insulator 48 seals the bottom of the housing preventing fluid from entering the region surrounding loop 50. There are two microwave coupling assemblies consisting of housing 45, wire loop 50, wire lead 51, insulator 52, and connector or coupling 53. One of these assemblies is used for coupling microwave power into the resonator and the other is for coupling the power out. Two tubes 44 are provided for fluid inlet and outlet. Both tubes enter cylinder 11 tangentially causing the fluid to spin about center conductor 40. The fluid motion prevents the heavy particles from settling in cylinder 11.

While fluid is flowing through microwave resonator 10, the voltage is applied by an alternating high-voltage power supply 54 connected to lead 47. The resulting charge on center conductor 40 results in a radial electric field, which aligns elongated conducting particles 60 along the radial field lines. The microwave electric field, which is also aligned along radial lines, generates microwave currents in the elongated particles 12. The current dissipates the microwave energy and lowers the resonator Q. When the voltage on center conductor 40 passes through zero, particles which were aligned radially are swept out of the resonator because of the fluid flow. New particles entering the resonator will be randomly aligned, since not as many will be aligned with the microwave field. The microwave currents generated in misaligned particles is much smaller than those generated in aligned particles and thus, less microwave energy is dissipated. In this manner the dissipation of microwave energy is modulated at the frequency of the high-voltage power supply. The modulation is sensed by a change in the microwave power coupled out through wire loop 50.

Microwave generator 28 provides radiation at a power level of about 10 milliwatts (mw). Frequency shifter 46 steps the frequency in large increments to coarsely tune oscillator 28 to the various modes of the resonator. In effect, frequency shifter 46 enables the logic unit 30 to select various resonator modes. Frequency modulator 53, operated by driver 48, alternately varies the frequency of the microwave radiation by small amounts before it is sent to the input coupling loop of microwave resonator 10. The small frequency variation is performed at a rate of several tens of kilo-hertz, and its amplitude is sufficient to ensure that the frequency of generator 28 plus the change in frequency due to the modulator 53 equals the resonant frequency of the selected mode for microwave resonator 10 during some part of the modulation cycle. The center conductor within coaxial microwave resonator 10 is charged with an alternating high-voltage power supply 54 whose frequency is controlled by driver 59. A typical frequency might be 10 Hz.

A microwave receiver 55 recovers the frequency modulation signal whose amplitude and phase relative to the phase of the frequency modulator are affected by lubricating oil 12. Using the signal at the output of receiver 55, the phase information from frequency driver 48, and the phase information from external field driver 59, logic unit 30 calculates the resonant frequency and Q of the coaxial resonator 10. Both the resonant frequency and Q vary with the external field and this variation periodically is recorded and averaged by logic unit 30.

Method for Inferring Standard Fluid Maladies Fluid maladies are defects that appear as a result of fluid use. For example: the depletion of antioxidant is a malady; the presence of water in the oil is a malady; the depletion of detergent is a malady, as is the presence of wear particles. Equations can be written showing the effect of any particular malady on the measurements that will be made with the fluid monitor described above. It is a simple matter to infer the measurement if the malady is known. The inverse problem of inferring the malady from the measurement is more difficult because each equation contains many unknowns. Equation (1) is an example. It shows the volumetric concentration of conducting particles as a function of the measured change in Q ($\Delta Q$) wrought by the particles.

$$\frac{V_p}{V_c} = \frac{3(1+E_l)}{4\pi\Delta Q(\chi''_{ee} + E_l\chi''_{me})} \quad (1)$$

Where:

$\chi''_{ee}$=imaginary part of the effective electric susceptibility, and $\chi''_{me}$=imaginary part of the effective magnetic susceptibility.

$E_l$=dielectric constant of the fluid alone.

Note that equation (1) can not be solved unless $\chi''_{ee}$, $\chi''_{me}$ and $E_l$ are known. $\chi''_{ee}$ depends on the aspect ratio of the particle, its length, and conductivity, while $\chi''_{me}$ depends on the particle's magnetic permeability. The number of unknowns is not a serious barrier since the number of variables under the control of the monitoring system can easily give rise to the required number of equations. The real problem is created by the likelihood that the equations do not describe all of the important effects. For example the effect of the dissolution of metal wear particles in the fluid by the action of water and acid would not be modeled by (1). The dissolved metal might reduce the Q misleading the user of (1) into inferring an incorrect metal concentration.

In view of the complexity of used-fluid mixtures, a better way to infer the malady is to consider the monitoring system output as a signature or fingerprint of a malady. The malady is identified by matching the fingerprint with a known fingerprint. A data base of known fingerprints is established by comparing standard laboratory results for samples of used fluid against the fingerprints made by this monitoring system on the same samples. For the approach to be effective, the finger prints must be rich in detail.

The monitoring system described above creates a rich fingerprint of the fluid condition every few seconds. The richness accrues from the number of variables under the control of logic unit 30—external frequency, external field amplitude, and resonator mode. With these variables, logic unit 30 creates the following four curves for each resonator mode accessed.

1. Q as a function of external field strength
2. Resonant frequency as a function of external field
3. The change in Q over an external field cycle as a function of external field frequency.
4. The change in resonant frequency over an external field cycle as a function of external field frequency.

Typically frequency shifter 46 can generate frequencies for three different resonator modes, giving rise to a finger print consisting of twelve curves.

Fingerprinting

Logic unit 30 orchestrates the taking of data that results in the set of curves that make up the finger print of a fluid malady. The unit systematically changes the variables under its control and records the output of receiver 55 in response to each variable change. For the recording and subsequent curve plotting, the logic unit converts the analog signal from the receiver to digital form. It does this with the use of a digitization clock which enables the unit to periodically measure the signal an integral number of times during each frequency-modulation cycle controlled by driver 48. Each measurement is recorded digitally in sequential memory bins. In this manner the smooth curve representing the microwave energy in the resonator as a function of time, as presented by the receiver, is converted to a set of discrete points. Since the digitization clock is phase locked to the microwave frequency driver 48, there is always a one-to-one relation between the microwave frequency and the memory bin number.

Points of the received signal are added to sequential memory bins until the signal occurring over a complete external-field cycle (driver 59) has been recorded. A great increase in precision is achieved by averaging the signal over many external field cycles. To reduce the memory requirement, the data from each succeeding cycle is added bin-for-bin to the data from all the preceding cycles. In other words, at the beginning of a new external-field cycle, the first measurement is digitized and added to the data in bin number one, the second measurement is added to the data in bin number two, and so forth. To ensure that a particular bin always corresponds to a particular time in the cycle, the external-field driver 59 must be phase locked to the microwave frequency driver 48 which is, in turn phase locked to the digitization clock.

After adding data for a specified number of external field cycles, software in logic unit 30 analyzes the data. A plot of the data against its sequential bin number would produce a graph consisting of a high-frequency periodic curve confined within a slowly varying sinusoidal envelope. The high-frequency period is controlled by driver 48, and the curve shape is formed from a series of lorentzians (inverted V's). Logic unit 30 begins its analysis by least-square fitting a lorentzian function to each recorded curve. The fit is performed in software by varying the two parameters that determine the position of the peak and the width of the curve. These correspond to the Q and the resonant frequency of the coaxial resonator at a particular value of the external field. When the optimum fit is achieved, the resulting Q and resonant frequency are recorded. Thus, each analysis event produces a table of resonant frequency and Q versus external field strength. The table's data is stored in an external medium not necessarily part of said fluid monitoring system.

Since logic unit 30 orchestrates the setting of the resonator mode (via frequency shifter 46) and the setting of the external-field frequency, the unit can associate the table with the known mode and external-field frequency. Once such a table is completed, the logic unit 30 increments either the external field frequency or the mode, and repeats the process to generate another table. These tables when plotted, form the curves described above; and thus, are themselves the required fingerprint. Once the tables are recorded on an external medium, the fingerprint is available for an external computer to perform a match. Even in the absence of an external computer, logic unit 30 will have enough built-in memory to compare the most recent finger print with the print of clean fluid and issue a warning if the prints differ by a specified amount.

Effect of Specific Maladies on Finger Prints

The effect of some specific maladies on the characteristic curves or fingerprints of a fluid can be mathematically modeled. The models are useful for estimating the sensitivity of fingerprints to the maladies. First the relation between resonant frequency and fluid dielectric constant will be described, and then the dependence of Q on the concentration, shape, and conductivity of metallic wear particles will be revealed.

Antioxidant Depletion

The dielectric constant of a fluid is sensitive to the concentrations of polar molecules in the fluid. These might be present as a result of expendable additives such as detergent or antioxidants. They may also be present as a result of contamination by water in water-cooled systems. The dielectric constant of a fluid depends on the average polarizability of its molecules. This is a result of the asymmetric charge distributions in the molecules which allow the molecules to store energy by stretching in an external electric field. In the alternating field of a microwave in coaxial microwave resonator 10, the time required to stretch the polar molecule effects wave phase velocity. This is manifested by a shift in resonant frequency. New, uncontaminated oil is relatively non-polar; and thus, has a small dielectric constant E of approximately 2.4. As the antioxidants are used up, the concentration of more polar molecules increases. The E of oil, consisting of a solution of oxidized normal oil, increases linearly with the concentration of oxidized oil. The resonant frequency of a particular resonator mode depends on the dielectric constant of the fluid according to (2):

$$\frac{\Delta f_r}{f_r} = -\frac{\Delta E}{2E} \quad (2)$$

Here $\Delta f_r$ is the change in resonant frequency and $f_r$ is the resonant frequency, while $\Delta E$ is the change in dielectric constant. Changes in $f_r$ can be measured to a precision of about 20 ppm with inexpensive microwave oscillators. This precision is sufficient for detecting changes in the work load of an operating engine. As an example, consider the lubricating fluid in an aircraft. When the pilot increases throttle, the bearings warm up increasing the oxidation rate of the lubricant. Hence, the E increases and the resonant frequency shifts. Logic unit 30's table of resonant frequencies against external field values will show an increase at all values of the external field. This then constitutes the finger print of a hard working engine, not necessarily the print of a malady. However, if the resonant frequency fails to recover after the engine cools down, then a case might be made for changing the oil since the fingerprint would then match that of an oil whose antioxidant is depleted.

Conducting Particles

The presence of conducting particles in coaxial microwave resonator 10 changes the Q according to the following equation:

$$\Delta \frac{1}{Q} = -\frac{4\pi V_p}{3(1+E_l)V_c} (\chi''_{ee} + E_l \chi''_{mi}), \quad (3)$$

Where:

$\chi''_{ee}$ = imaginary part of the effective electric susceptibility, and $\chi''_{me}$ = imaginary part of the effective magnetic susceptibility.

$E_l$ = dielectric constant of the fluid alone.

Effective susceptibilities are related to normal susceptibilities through the depolarization factor which accounts for the difference between the field immediately external to the particles and the fields within the particles. The depolarization factor depends on the shape of the particles. The relation between the imaginary part of the effective magnetic susceptibility and the complex components of susceptibility Xm is given by the following equation:

$$\chi''_{me} = \frac{\chi''_m + 4\pi L(\chi'^2_m + \chi''^2_m) - i\chi''_m}{(1 + 4\pi L\chi'_m)^2 + (4\pi L\chi''_m)^2} , \quad (4)$$

where the singly-primed quantities are real components, double-primed components are the imaginary, and L is the depolarization factor. The same equation can be used to determine the imaginary part of effective electric susceptibility (X"ee) by replacing the subscript m with an e. For cylindrically shaped particles, with the magnetic component of the microwave field parallel to the cylindrical axis:

$$L = \left(\frac{d}{l}\right)^2 \left[\ln\left(\frac{2l}{d}\right) - 1\right], \quad (5)$$

where d=particle diameter, and the lower case L=particle length. For disc-like platelets, whose surface is parallel to the magnetic component of the microwave field, $$L = \frac{\pi t}{4a} \left(1 - \frac{4t}{\pi a}\right), \quad (6)$$

where t is the thickness of the plate and a is its diameter (t<<a).

The material properties are directly related to the effective susceptibilities. One of the most important material properties is the particle conductivity which determines the imaginary components of effective electric susceptibility:

$$\chi''_e = \frac{E''_l + \frac{2s}{f_r}}{4\pi} \cong \frac{s}{2\pi f_r} , \quad (7)$$

where s is the conductivity and E" is the imaginary component of the dielectric constant of the lubricating fluid 12. An estimate for the sensitivity of the instrument can be made using the following values, typical for hardened steel: X'ee= 0.34, X"me=0.32, Em=2 and s=100,000 mho. In forming this estimate, 1 ppm, will be assumed as the minimal detectable change in Q, (obtained with averaging techniques that make use of locked frequency relations between the microwave frequency driver 48 and the fixed field driver 59). Using the above values in (3), it is clear that a change in particle concentration ($V_p/V_c$) of 1 ppm (parts per million) will make a detectable change to the table of Q against external field strength; and thus, affect the fingerprint.

Noise in the tabulated values of Q is another useful fingerprint feature. The wear debris consists of a combination of fluid-like particles too small to be filtered out and a sparse concentration of larger particles that are filterable. Since the lubrication fluid condition monitor shown in FIG. 1, is inserted in scavenge-oil line 14, it will sense the large particles as they are produced by the bearing and before they are filtered out. Regardless of particle size, microwave fields will induce currents in the conducting particles and these currents will dissipate energy through ohmic losses which will change the Q of coaxial microwave resonator 10 inversely with the volume of conducting particles in the resonator.

If the volume of the small particles in coaxial microwave resonator 10 is much less than the volume of a single large particle, the Q will deviate in a random manner from one measurement to the next depending on the size of the particle that happens to be in the resonator when the measurement is performed. On the other hand, if the volume of the small particles is much larger than the volume of the single large particle, then the signal will barely be affected by the large particle. However, this situation is unlikely since lubricating fluid 12 should be changed before this condition occurs. Reality lies between these two extremes. A low, relatively settled, steady signal level exists for normal wear due to the fine particles. When abnormal wear occurs, the signal becomes noisy with the low level from the fine particles defining the floor of the noise fluctuations. By filtering out the steady component, a signal sensitive only to large particles is obtained and vice versa. Thus, the fingerprint of large particles is noise.

The viscosity of the oil is indicated by the time it takes to rotate asymmetrical metal particles in the alternating electric field or magnetic field. If the field frequency is too high, the particles will not have time to turn during the cycle and thus, the change in the Q of coaxial microwave resonator 10, over a cycle will be zero. The curve of $\Delta Q$ versus external-field frequency will be similar to that shown in FIG. 4. The frequency at which the knees in the curve occur will be sensitive to the viscosity, and the sharpness of the knees will depend on the breadth of the distribution of particle aspect ratios. These features of the fingerprint will enable matches to be made that will lead to a determination of viscosity.

A variation of the invention, comprised of a microwave resonator constructed from stripline elements on a printed circuit board, is shown in FIG. 3. This alternative embodiment utilizes a capacitor and an inductor whose values depend upon the properties of the surrounding materials. The circuit is comprised of a interdigitated capacitor 34 and an inductor 36 mounted on a printed circuit board 38. The advantage of the stripline sensor is the substantial reduction in size over the waveguide technique of FIG. 1. The stripline sensor of FIG. 3 could be on the order of 1 mm (millimeter) which could greatly expand the number of applications suitable for the sensing system. However, the stripline sensor might be less sensitive because of losses due to the material of circuit board 38 in the circuit.

The system of FIG. 3 comprises a series planar tank circuit consisting of single loop conductor 36 and interdigitated capacitor 34. The size of the stripline sensor will depend upon the resonant frequency chosen. One example would be to provide an inductor 36 having a 1 mm radius, with an inductance of the order of several nH and a interdigitated capacitor 34 of 1 mm by 4 mm with 20 fingers, 100 micrometers (um) wide, spaced at 100 um giving a capacitance of C=1 pF, leading to resonant frequencies in the neighborhood of 5 GHz.

When the stripline sensor of FIG. 3 is immersed in lubricating fluid 12, the real and imaginary parts of the impedance are altered. This alteration causes the phase and intensity of microwaves reflected from the stripline to change. These changes are measured and lubricant properties can be determined from the measurements.

In yet another variation of the invention, a stripline transmission line may be printed on a circuit board which is immersed in the fluid. The Q and resonant frequency of the transmission line resonator will be altered by the surrounding fluid just as it was for the lumped circuit stripline resonator shown in FIG. 3.

Regardless of the details of sensor construction, the method of using either an electric field or a magnetic field or both, to change the orientation of asymmetrical wear products in the vicinity of sensors, is unique and useful. The processing of the field produced provides a method to determine the fluid viscosity, distribution of particle sizes and whether particles are ferrous or non-ferrous conducting particles.

Thus, there has been described, a unique lubricating fluid monitoring system for determining the chemical properties and concentration of debris in the fluid. In the first embodiment, a coaxial microwave resonator is positioned in a line through which lubricating oil from a bearing or other part flows. A microwave oscillator is used to apply microwave power to the coaxial microwave resonator. The resonator Q and resonant frequency are affected by changes in the lubricating fluid. Thus measurement of Q and resonant frequency provide a means for determining the properties of the fluid. In a second embodiment of the invention, a lumped resonator printed on a circuit board is used as the sensor. Still another variation of the invention, a transmission line printed on a circuit board (stripline) is used as a microwave resonator to produce a sensor for determining the changes in chemical composition and debris in a lubricating fluid.

This invention is not to be limited by the embodiment shown in the drawings and described in the description which is given by way of example and not of limitation, but only in accordance with the scope of the appended claims.

What is claimed:

1. A system for monitoring the condition of lubricating/hydraulic fluid comprising:

a lubricating/hydraulic system having lubricating/hydraulic fluid flowing in a conduit;

a microwave stripline resonator immersed in the fluid flowing in said conduit;

said microwave stripline resonator comprised of a loop inductor and interdigitized capacitor;

microwave oscillating means connected to said microwave resonator to apply microwave frequency radiation to said resonator;

means of r applying a varying electric or magnetic field to said lubricating/hydraulic fluid;

detecting means detecting changes in microwave radiation build-up within said microwave resonator;

logic means connected to said detecting means to analyze said changes in s aid microwave radiation;

said logic means determining the chemical and physical properties of said lubricating/hydraulic fluid from said changes in microwave radiation;

whereby said lubricating/hydraulic fluid monitoring system provides advance warning of deterioration of mechanical parts and helps pinpoint failure when it occurs.

2. The system according to claim 1 in which said capacitor has a capacitance of approximately 1 pF.

3. The system according to claim 1 in which said inductor is a 1 mm loop inductor.

4. The system according to claim 1 in which said microwave resonator has a resonant frequency of approximately 5 GHz.

5. The system according to claim 1 in which said logic means determines the dielectric constant of said lubricating/hydraulic fluid.

6. The system according to claim 1 in which said logic means determines concentration of conductive particles in said lubricating/hydraulic fluid.

7. The system according to claim 6 in which said logic means determines the concentration of conductive particles in said lubricating/hydraulic fluid from a data base made by comparing measurements made with said system to measurements made with well established laboratory instruments.

8. The system according to claim 6 in which said logic means determines the concentration of ferromagnetic particles in said lubricating/hydraulic fluid.

9. The system according to claim 8 in which said logic means measures the concentration of ferromagnetic particles in said lubricating/hydraulic fluid from a data base made by comparing measurements made with said system to measurements made with well established laboratory instruments.

* * * * *